(12) United States Patent
Howes, Jr. et al.

(10) Patent No.: US 7,126,343 B1
(45) Date of Patent: Oct. 24, 2006

(54) CONDUCTIVITY PROBE WITH TOROID KEEPER

(75) Inventors: Ronald Bruce Howes, Jr., Minneapolis, MN (US); John Ellwood Thomas, River Falls, WI (US); Paul Joseph Pankratz, Lakeville, MN (US)

(73) Assignee: Ecolab Inc., Eagan, MN (US)

( * ) Notice: Subject to any disclaimer, the term of this patent is extended or adjusted under 35 U.S.C. 154(b) by 0 days.

(21) Appl. No.: 11/191,667

(22) Filed: Jul. 27, 2005

(51) Int. Cl.
*G01N 27/02* (2006.01)

(52) U.S. Cl. .................................... 324/446; 336/229
(58) Field of Classification Search ............... 324/445, 324/446; 336/229
See application file for complete search history.

(56) References Cited

U.S. PATENT DOCUMENTS

| | | | |
|---|---|---|---|
| 2,435,043 A | 1/1948 | Lehde et al. | 73/861.11 |
| 2,987,668 A | 6/1961 | Gondouin | 324/342 |
| 3,396,331 A | 8/1968 | Sperry, III | 324/445 |
| 3,806,798 A | 4/1974 | Gross | 324/445 |
| 4,220,920 A | 9/1980 | Gross | 324/442 |
| 4,733,798 A | 3/1988 | Brady et al. | 222/23 |
| 4,816,758 A | 3/1989 | Theissen et al. | 324/204 |
| 5,077,525 A * | 12/1991 | West et al. | 324/445 |
| 5,157,332 A | 10/1992 | Reese | 324/445 |
| 5,556,478 A | 9/1996 | Brady et al. | 134/18 |
| 5,681,400 A | 10/1997 | Brady et al. | 134/18 |
| 6,995,563 B1 * | 2/2006 | Talutis | 324/439 |

* cited by examiner

*Primary Examiner*—Walter Benson
(74) *Attorney, Agent, or Firm*—Shumaker & Sieffert, P.A.

(57) ABSTRACT

An apparatus and associated process for constructing a conductivity probe are disclosed. The conductivity probe includes at least two magnetic circuits in toroidal shape. Each of these "toroids" includes a ferrite core around which is wrapped a conductive wire (i.e., coil winding). To construct the conductivity probe, a toroid keeper having an upper annulus and a lower annulus separated by a spacer is provided. One of the two toroids is set on the upper annulus and the other toroid is set on the lower annulus. Connection leads extending from the coil wrappings of the toroids are routed from the keeper through wiring channels build into an elongated neck coupled to the keeper. The connection leads terminate at the distal end of the elongated neck relative to the keeper for connection to a controller.

15 Claims, 6 Drawing Sheets

US 7,126,343 B1

CONDUCTIVITY PROBE WITH TOROID KEEPER

TECHNICAL FIELD

The present invention relates generally to measuring conductivity of fluids, and more particularly to an instrument to accomplish such measuring, the instrument being referred to in the art as a conductivity probe.

BACKGROUND

Conductivity probes are used in numerous applications to measure the conductivity of fluids for use in various types of analyses. For example, conductivity probes are commonly used in connection with warewashing operations to monitor the conductivity of a chemical solution being applied to eating and kitchen utensils. In such uses, the conductivity of the chemical solution represents the ionic and/or acidic concentration within the chemical solution relative to pure water, and thus indirectly indicates the percent concentration of one or more component chemical products making up the chemical solution. The use of conductivity probes to facilitate warewashing operations is described in greater detail in U.S. Pat. No. 4,733,798, issued to Brady et al. on Mar. 29, 1988.

Conventional design for conductivity probes involves placing a first magnetic circuit in an arrangement relative to a second magnetic circuit. The magnetic circuits are typically toroidal in shape, and consequently have an inner circumference and an outer circumference. For this reason, these magnetic circuits are commonly referred to as "toroids." Toroids include a ferrite core between the inner and outer circumferences around which wrapped a conductive wire, which is commonly referred to as a "coil winding."

In operation, both toroids of a conductivity probe are submerged in a fluid and a current is induced in the wire of the first toroid, thereby generating a perpendicular electric field within the fluid. This electric field induces a current in the fluid that passes through the center of the second toroid. The ferrite core of the second toroid is consequently magnetized thus generating a current in the associated coil winding. The resultant electrical output of the wire winding of the second toroid indicates the conductivity of the fluid. Such a design is very typical of most conductivity probes on the market with the first magnetic circuit being referred to as a "driving toroid" and the second magnetic circuit being referred to as a "sensing toroid." For example, U.S. Pat. No. 5,157,332, issued to Philip Reese on Oct. 20, 1992, describes one such design for a conductivity cell as well as an improved design having three toroids.

Most conductivity probes include a housing that protects the driving and the sensing toroids from their applicable environment. More particularly, the housing prevents any fluid being measured from entering the toroid wirings, while at the same time, providing a medium through which electric fields may pass without substantial field loss. FIG. 1 depicts an exemplary housing 102 in connection with an illustration of the construction of a conventional conductivity probe 100.

The conductivity probe 100 is constructed using a manual process in which a first toroid 108 and a second toroid 110 are inserted into a toroidal shaped compartment 103 of the housing 102. The toroidal shaped compartment 103 includes an outer circumferential wall 104 and an inner circumferential wall 105, thereby forming a passageway 106 that enables fluid to pass directly through the toroidal shaped compartment 103. The inner circumferential wall 104 and the outer circumferential wall 105 are spaced with respect to one another to accommodate the toroids 108 and 110.

Potting compound, which is not shown in FIG. 1, is commonly used to fill the empty space in the toroidal shaped compartment 103 between and around the toroids 108 and 110. After the toroids 108 and 110 and the potting compound have been placed in the toroidal shaped compartment 103, a toroidal cap 115 is welded on the compartment 103 such that the compartment 103 is enclosed to protect the windings 112 and 114 of the toroids 108 and 110 from being directly exposed to a fluid environment.

As noted above, each toroid 108 and 110 includes a ferrite core 109 and 111 around which is wrapped a conductive wire thus forming windings 112 and 114. The wires each include a pair of connection leads 116 and 118. A first pair of connection leads 116 extends from the first toroid 108 as a part of the conductive winding 112 wrapped therearound. A second pair of connection leads 118 extends from the second toroid 110 as a part of the conductive winding 114 wrapped therearound.

The conductivity probe 100 includes a hollow neck 107 through which the first and second connection lead pairs 116 and 118 are loosely fed while the toroids 108 and 110 are being placed into the toroidal shaped compartment 103. The connection lead pairs 116 and 118 provide an electrical communication interface to a controller (not shown), such as, for example, a warewash controller, at the distal end of the hollow neck 107 relative to the toroidal shaped compartment 103. Using these connection leads 116 and 118, the controller operates the conductivity probe 100 in its intended manner, i.e., to monitor conductivity of a fluid environment. More particularly, a first pair of the connection leads 116 provides an electrical input interface to the controller while a second pair of the connection leads 118 provides an electrical output interface to the controller. That is, current induced in the first pair of connection leads 116 by a controller is communicated to the first toroid 108, which consequently generates a perpendicular electric field in proximity to the toroidal shaped compartment 103. The generated electric field is thus applied to the fluid environment in which the toroidal shaped compartment 103 is submerged while the current is being induced in the first pair of connection leads 116.

The electric field, which affects any ions and other particles having electrical characteristics present in the fluid environment, excites the second toroid 110 thereby generating a current within the coil winding 114 that is communicated by way of the second pair of connection leads 118 to the controller. The electrical output at the termination of the second pair of connection leads 118 indicates the conductivity of the fluid environment, as measured based on the degree that the electric field affects the ions and other particles in the fluid environment.

The above-described method for constructing the conductivity probe 100 shown in FIG. 1 has several drawbacks that seriously undermine the accuracy of measurements taken by the probe 100 over its effective lifetime. While potting compound provides for a decent medium for physically separating the toroids 108 and 110 from one another and the inner circumferential wall 105, it does not provide a tight, rigid contact with respect to the conductive windings 112 and 114. Therefore, over the lifetime of the probe 100, the spacing of the windings 112 and 114 around the ferrite core inevitably becomes inconsistent and the windings tend to loosen. Furthermore, keeping in mind that it is optimal to have the windings 112 and 114 cover the entire 360 degrees around the ferrite cores 109 and 111, the above-described design tends to result in relatively wide separation of the windings 112 and 114 at or around the proximal of the connection lead pairs 116 and 118 relative to the toroidal shaped compartment 103. In addition, loose placement of the connection lead pairs 116 and 118 within the hollow neck 107 often results in electrical interference, or "noise," between the lead pairs 116 and 118 when carrying current.

SUMMARY OF THE INVENTION

In accordance with the present invention, the above and other problems are solved by a keeper having an upper portion and a lower portion separated by a spacer. The keeper is used to construct a conductivity probe having at least two magnetic circuits, each circuit having an inner circumference and an outer circumference. The upper and lower portions are sized to fit the two magnetic circuits in that, when set on the keeper portions, the inner circumference of each of the magnetic circuits contacts the outer surface of the respective keeper portions.

In an embodiment, the magnetic circuits are toroids and the keeper is thus a toroid keeper having an upper annulus, a lower annulus and a spacer that separates the upper annulus from the lower annulus. The upper annulus is sized to hold the first toroid on the keeper. Likewise, the lower annulus is sized to hold the second toroid on the keeper.

Another embodiment of the present invention is directed to an apparatus for constructing a conductivity probe. The apparatus includes a keeper and an elongated neck that is coupled to and extends from the keeper. The elongated neck therefore includes a distal end and a proximal end relative to the keeper. In this embodiment, the elongated neck carries wiring from each of the magnetic circuits set on the keeper from the proximal end to the distal end.

In yet another embodiment, the present invention is directed to a method for constructing a conductivity probe using a keeper having an upper portion and a lower portion separated by a spacer. The upper and lower portions of the keeper both have an inner and an outer surface. The method according to this embodiment involves setting a first magnetic circuit having on the upper portion of the keeper and setting a second magnetic circuit having an inner circumference and an outer circumference on the lower portion of the keeper. After the circuits are set, the inner circumferences of the circuits contacts an outer surface of the upper and lower portions of the keeper over at least 181 radial degrees.

These and various other features as well as advantages, which characterize the present invention, will be apparent from a reading of the following detailed description and a review of the associated drawings.

BRIEF DESCRIPTION OF THE DRAWINGS

FIG. 2a depicts a top view of an apparatus for conducting a conductivity probe in accordance with an embodiment of the present invention.

FIG. 2b depicts a bottom view of the apparatus shown in FIG. 2a.

DETAILED DESCRIPTION

Figure 1:
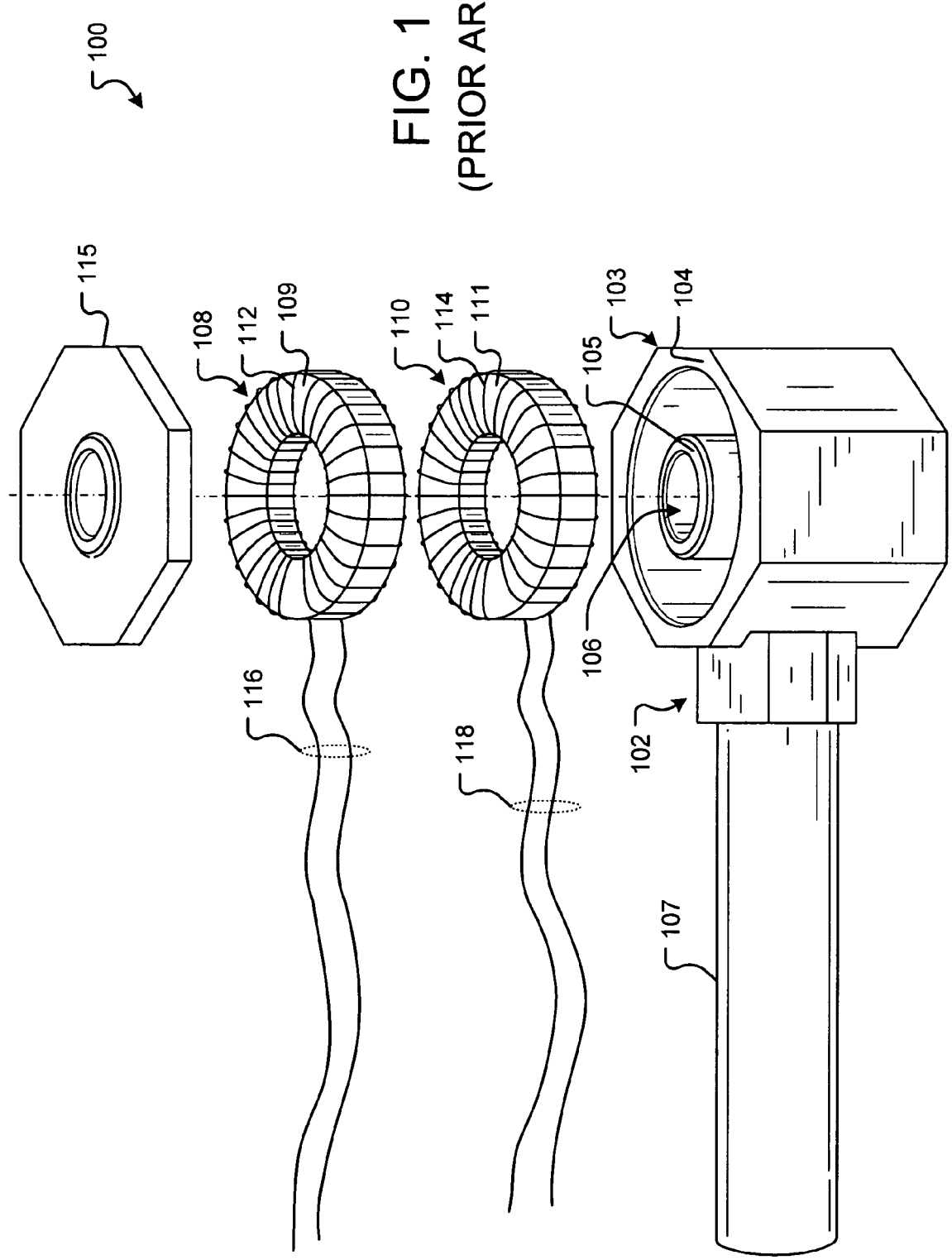
FIG. 1 illustrates construction of a conventional conductivity probe in accordance with well-known procedures.

The present invention and its various embodiments are described in detail below with reference to the figures. When referring to the figures, like structures and elements shown throughout are indicated with like reference numerals. Objects and structures depicted in the figures that are covered by another object, as well as the reference annotations thereto, are shown using dashed lines.

Generally speaking, the present invention relates to an apparatus and an associated process for constructing a conductivity probe. The conductivity probe includes at least two magnetic circuits. In accordance with an exemplary embodiment, the present invention is described herein with the magnetic circuits being toroidal in shape, and thus referred to as "toroids." It should be appreciated, though, that the magnetic circuits may take any other shape, and indeed, any such shape is contemplated within the scope of the present invention.

Conductivity probes constructed according to the present invention may be used in any conventional application in which prior art conductivity probes are used. Exemplary applications in which the conductivity probes are useful include, but certainly are not limited to, warewashing operations, laundry operations, clean in place systems, chemical dispense systems and the like. Indeed, the conductivity probes described herein may be used in any application in which it is desirable to measure conductivity of any type of fluid.

Figure 2:
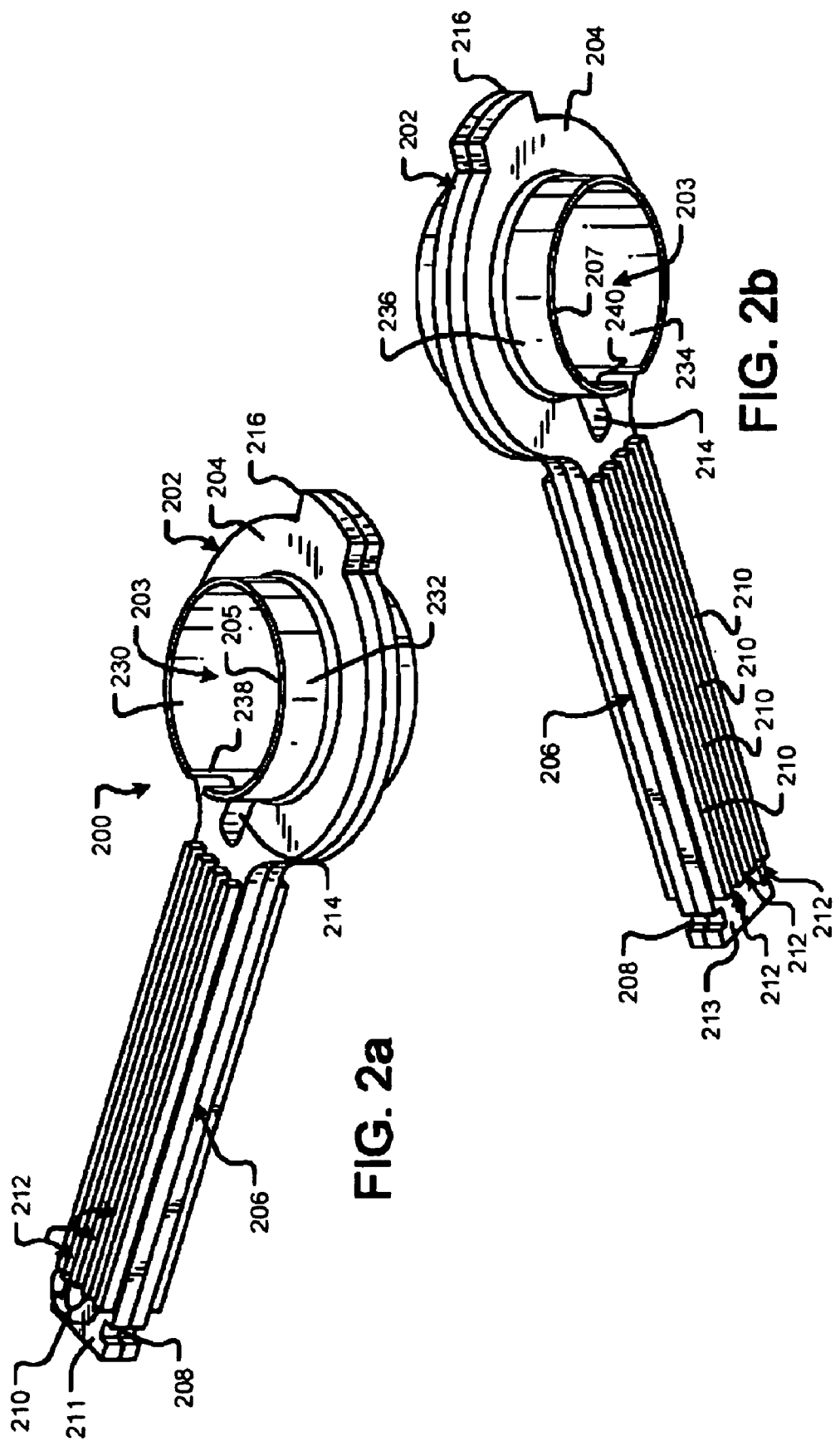

FIGS. 2a and 2b depict top and bottom views, respectively, of an apparatus 200 for constructing conductivity probes in accordance with an embodiment of the present invention. For nomenclature purposes only, the apparatus 200 is referred to herein as a "skeleton." In an embodiment, the skeleton 200 is formed of a plastic material, but alternatively, may be formed using other types of material that does not have magnetic properties such as, for example, polypropylene.

The skeleton 200 includes a keeper 202 and a neck 206. The keeper 202 includes a top centrally-apertured portion 205, a bottom centrally-apertured portion 207 and a disc-shaped spacer 204 physically dividing the top keeper portion 205 from the bottom keeper portion 207. In an embodiment, the centrally-apertured portions 205 and 207 take the form of ring of a predetermined height, as measured from the spacer 204. Even further, in an exemplary embodiment in which the keeper 202 is intended to keep toroids, the centrally-apertured portions 205 and 207 take the form of a circular ring having an inner surface 230 and 234 and an outer surface 232 and 236. Accordingly, the keeper 202 is referred to herein as a "toroid keeper" and the centrally-apertured portions 205 and 207 are referred to herein as a top, or upper, "annulus" 205 and a bottom, or lower, "annulus" 207. Those of skill in the art will appreciate that the centrally-apertured portions 205 and 207 may take any other shape as used for the magnetic circuits described herein in exemplary form as toroidal. Furthermore, it should be appreciated that the centrally-apertured portions 205 and 207, regardless of shape, may include one or more notches, such as the notches 238 and 240 shown in FIGS. 2a and 2b, respectively. That is, the top annulus 205 and the bottom annulus 207, although ring-shaped, may or may not include a contiguous circumference.

In yet another embodiment, the top annulus 205 and the bottom annulus 207 are sized to fit at least one toroid each, and therefore include a diameter substantially sized to match the inner diameter of the toroids that are intended to fit thereon. In this embodiment, the inner circumferences of the toroids that are intended to fit on the toroid keeper 202 contact the outer surfaces 232 and 236 of the annuli 205 and 207 over an a majority of 360 degrees, i.e., the inner circumferences of the toroids contact the outer surfaces 232 and 236 over at least 181 degrees.

The disc-shaped spacer 204 includes a central aperture, which in combination with the top (205) and the bottom (207) annuli, forms a passageway 203 within an inner region of the toroid keeper 202, as shown in FIGS. 2a and 2b. In an embodiment, the disc-shaped spacer 204 provides an electrical shield between the toroids (not shown) set on the top annulus 205 and the bottom annulus 207. In this embodiment, the disc-shaped spacer 204 is therefore selected from a material operable to limit direct induction from the driving toroid (not shown) to the sensing toroid (not shown). Alternatively, the disc-shaped spacer 204 may be formed of the same material as the skeleton 200.

The neck 206 includes an upper surface 211 and a lower surface 213, each of which includes a plurality of wiring guides 210. The wiring guides 210 are positioned in spaced arrangement with one another to create channels 212 on the upper surface 211 and the lower surface 213 of the neck 206.

In addition to the above-noted features, the skeleton 200 also includes a cavity 214 for holding a sensor (not shown) for measuring temperature of a fluid environment in which the annulus 203 is submerged. Temperature sensors, commonly referred to as "thermo sensors," are widely known in the art and the cavity 214 may be sized to hold any such known thermo sensor. The skeleton 200 also includes two notches 208 and 216. A first notch 208 is used to tie down wiring (not shown) situated in the wiring channels 212 at the distal end of the skeleton 200 relative to the toroid keeper 202. A second notch 216 is located on a proximal end of the skeleton 200 relative to the toroid keeper 202 and used to position the skeleton 200 during molding processes. During such molding processes, the skeleton 200 is coated in an electrically transparent material that prevents fluid from entering the coil windings (e.g., conductive wires 112 and 114) of toroids fitted on the toroid keeper 202, while at the same time, providing a medium through which electric fields may pass without substantial field loss.

Figure 3:
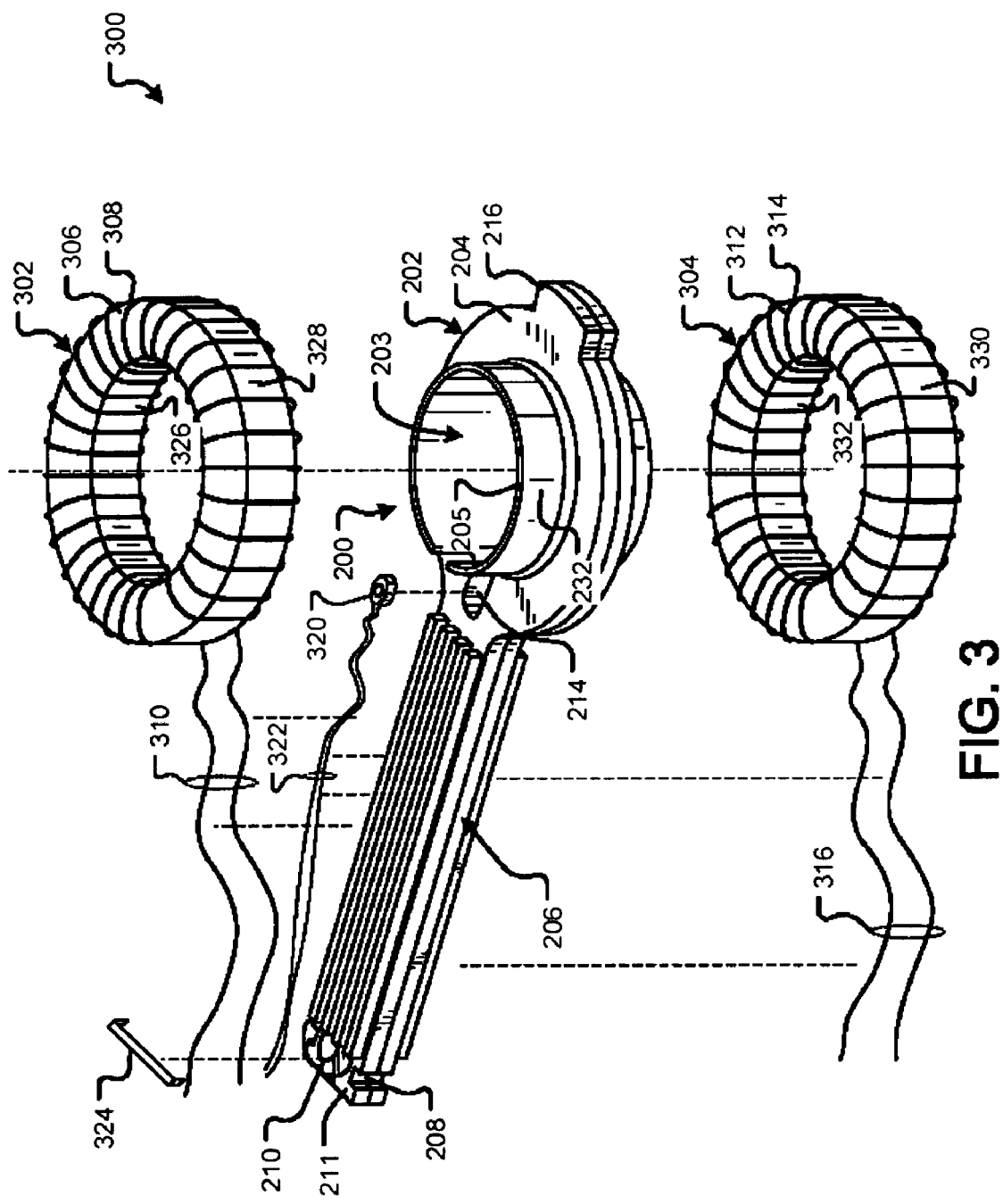
FIG. 3 is a functional diagram illustrating construction of a conductivity probe using the apparatus shown in FIGS. 2a and 2b in accordance with an embodiment of the present invention.
Figure 4:
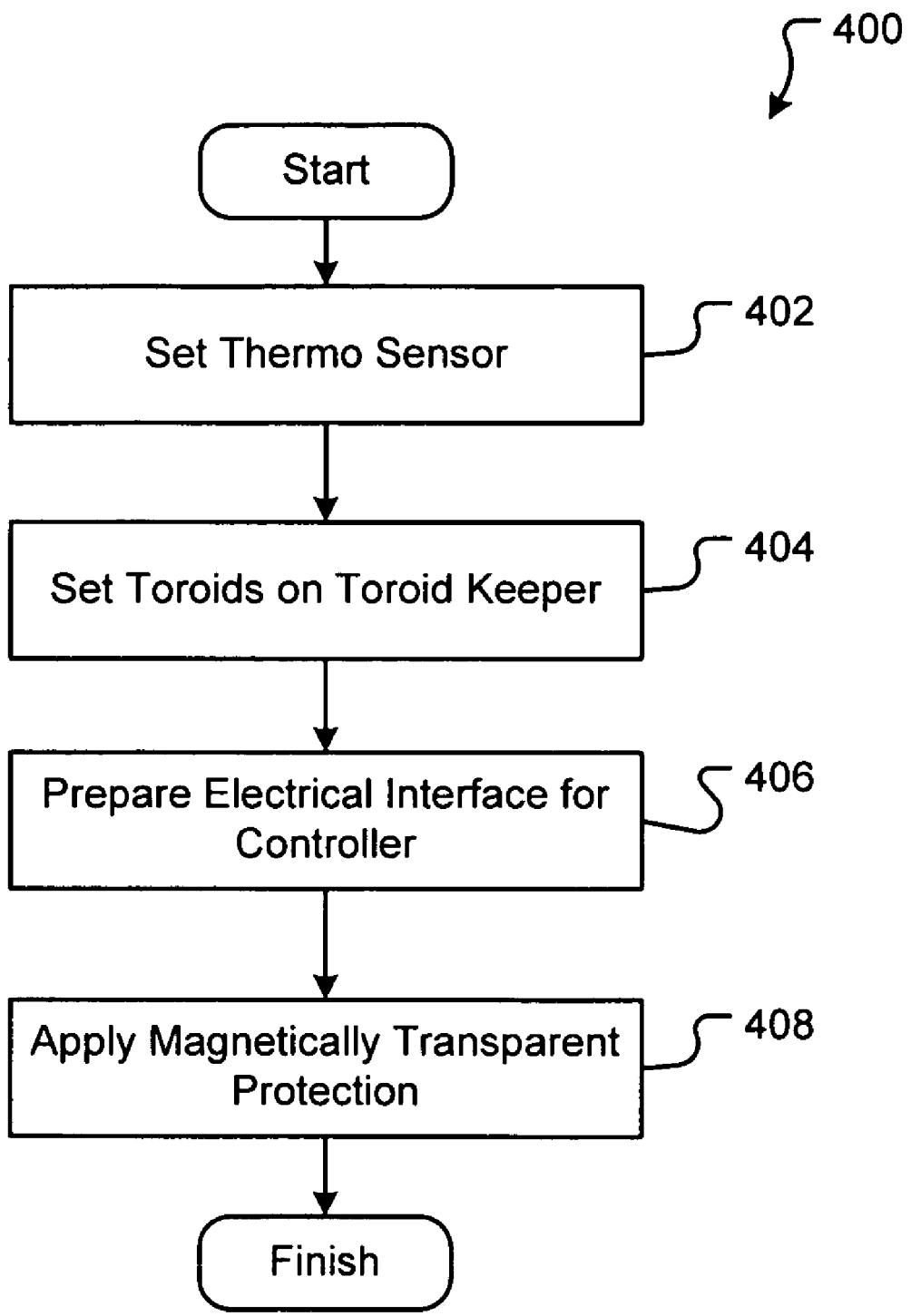
FIG. 4 is a flow diagram illustrating construction of a conductivity probe using the apparatus shown in FIGS. 2a and 2b in accordance with an embodiment of the present invention.

Turning now to FIGS. 3 and 4, construction of a conductivity probe 300 using the skeleton 200 of FIGS. 2a and 2b is shown in accordance with an embodiment of the present invention. Whereas FIG. 3 illustrates the construction process in accordance with this embodiment in functional diagram form, FIG. 4 illustrates this process in flow diagram form. The construction process is described herein and shown in FIG. 4 as being performed using a sequence 400 of manual actions made in connection with the skeleton 200. However, those of skill in the art will recognized that any such actions described in connection with this construction process may alternatively be performed by an analog or digitally controlled machine such as, for example, on an assembly line. Furthermore, the actual sequence in which the actions are performed is described herein in accordance with an exemplary embodiment. It should be appreciated that the actual sequence in which these actions are performed relative to one another may be altered or modified without departing from the scope of the present invention.

As shown collectively in FIGS. 3 and 4, the construction process begins with an action 402 that involves setting a thermo sensor 320 into the cavity 214. In an embodiment, the thermo sensor 320 is a thermistor having a pair of connection leads 322 operable to interface with a controller (not shown) utilizing the conductivity probe 300 in its intended manner, i.e., to monitor properties (e.g., temperatures and conductivity) of a fluid environment. For example, a warewash controller may interface with the pair of connection leads 322 in order to monitor the temperature of a chemical solution being used to clean kitchen and eating utensils. During construction of the conductivity probe 300 the pair of connection leads 322 is set in a wiring channel 212 on either the upper planar surface 211 or the lower planar surface 213 of the neck 206.

The next step of the construction process embodies an action 404 that involves setting toroids on the toroid keeper 202. As such, this action 404 includes sub-actions that involve placing a first toroid 302 on the top annulus 205 in contact with the top surface of the disc-shaped spacer 204 and a second toroid 304 on the bottom annulus 207 in contact with the bottom surface of the disc-shaped spacer 204. The thermo sensor 320 is consequently sandwiched between the first toroid 302 and the second toroid 304, thereby limiting movement of the thermo sensor 320 when the conductivity probe 300 operates in its intended environment.

As described in greater detail above, the first toroid 302 includes an inner circumference 326, an outer circumference 328, a ferrite core 306, a conductive coil winding 308 and a pair of connection leads 310 extending away from the first toroid 302. Likewise, the second toroid 304 includes an inner circumference 330, an outer circumference 332, a ferrite core 312, a conductive coil winding 314 and a pair of connection leads 316 extending away from the second toroid 304.

In accordance with an embodiment of the present invention, the top annulus 205 and the bottom annulus 207 are both sized such that the first toroid 302 and the second toroid 304, respectively, firmly contact the toroid keeper 202 thereby forming a tight contact medium with respect to the coil windings 308 and 314. In this embodiment, the first toroid 302 is situated around the top annulus 205 such that the inner circumference 326 of the first toroid 302 contacts the outer surface 232 of the top annulus 205 over a majority of 360 degrees, i.e., the inner circumference 326 of the first toroid 302 contacts the outer surface 232 of the top annulus 205 over at least 181 degrees. Likewise, the second toroid 304 is situated around the bottom annulus 207 such that the inner circumference 330 of the second toroid 304 contacts the outer surface 236 of the bottom annulus 207 over an entire 360 degrees.

Furthermore, in an embodiment, the heights of the top annulus 205 and the bottom annulus 207 relative to the disc-shaped spacer 204 are substantially equal to the thickness of the first toroid 302 and the second toroid 304, respectively. In this embodiment, the toroids 302 and 304 are substantially flush with the top and bottom annuli 205 and 207 when set on the toroid keeper 202.

After the toroids 304 and 306 are set on the toroid keeper 202, the next action 406 of the construction process involves preparing the electrical interfaces of the first toroid 302, the second toroid 304 and the thermo sensor 320 for connection to a controller. In an embodiment, this action 406 involves positioning each of the connection lead pairs 310 and 316 within a channel 212 on either the top surface 211 or the bottom surface 213 of the neck 206. This particular action 406 also involves securing the connection lead pairs 310 and 316 (extending from the coil windings 308 and 314) and the connection lead pair 322 (extending from the thermo sensor 320) within their respective channels 212 using tie downs, such as the tie down 324 shown for securing the connection lead pair 310 and the connection lead pair 322 within their respective channels 212 on the top surface 211 of the neck 206. Although not shown in FIG. 3, it should be appreciated that a similar tie down is employed to secure the connection lead pair 312 in its respective channel 212 on the bottom surface 213 of the neck 206. Once secured, the connection lead pairs 310, 316 and 322 are ready to be crimped, soldered or otherwise coupled to controller wiring for electrical interface therewith.

Figure 5:
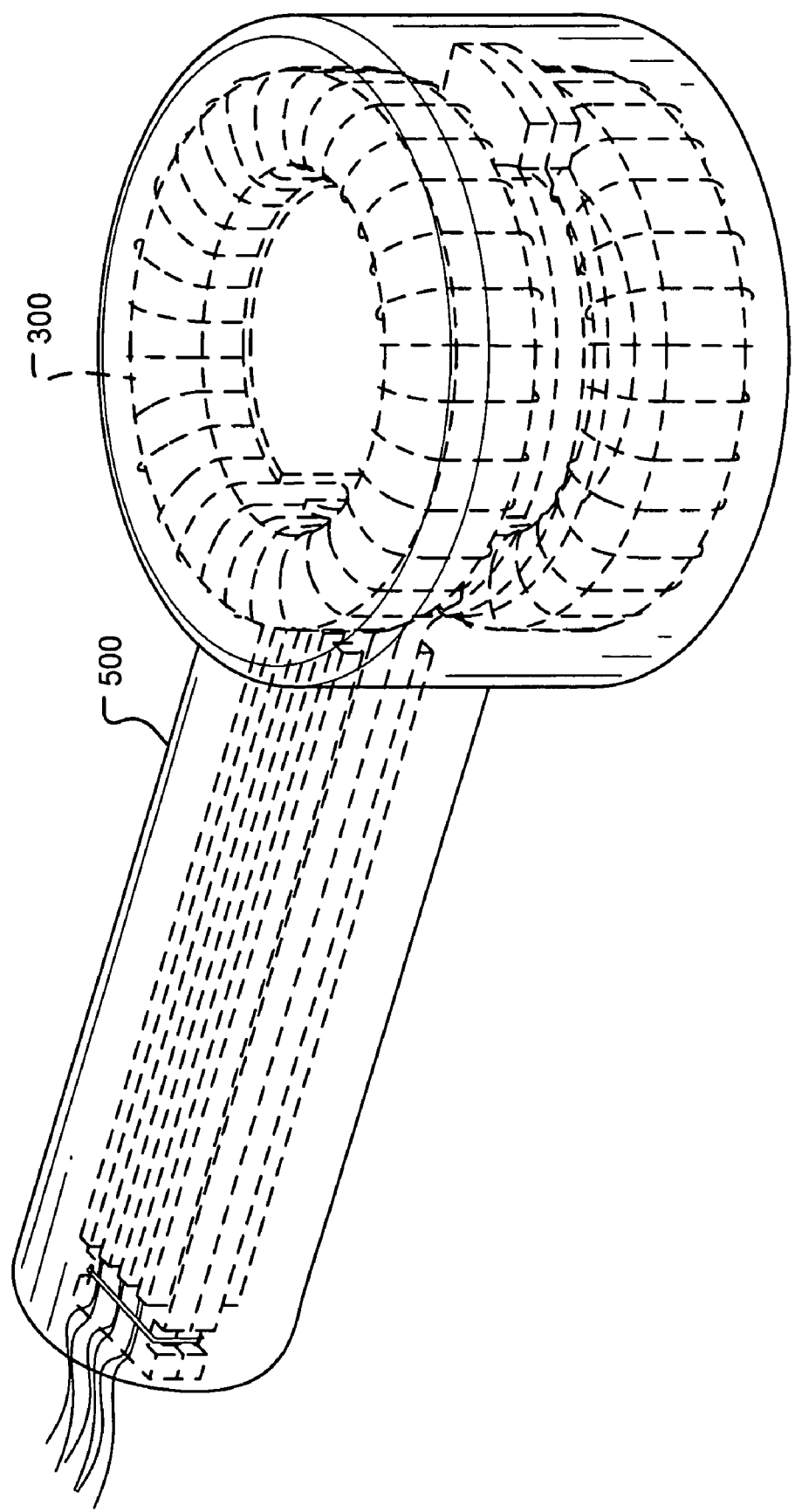
FIG. 5 depicts a conductivity probe constructed in accordance with the process illustrated in FIGS. 3 and 4, the conductivity probe having a housing in accordance with an embodiment of the present invention.

The next action 408 in the construction process involves protecting the conductive coil winding 308 of the toroids 302 and 304 from the fluids in which the conductivity probe 300 will be submerged. In accordance with an embodiment, this action 408 entails applying the conductivity probe 300 to a molding process wherein the conductivity probe 300 is dipped or otherwise coated with hot plastic, rubber or other suitable material that will dry to provide an electrically transparent coating over the probe 300. Any type of molding material that is operable (once dry) to prevent fluid from entering the coil windings 308 and 314, while at the same time, provide a medium through which electric fields may pass without substantial flux loss are contemplated within the scope of the present invention. In accordance with another embodiment, this action 408 entails fitting an electrically transparent housing 500 over the conductivity probe 300, as shown in FIG. 5.

Figure 6:
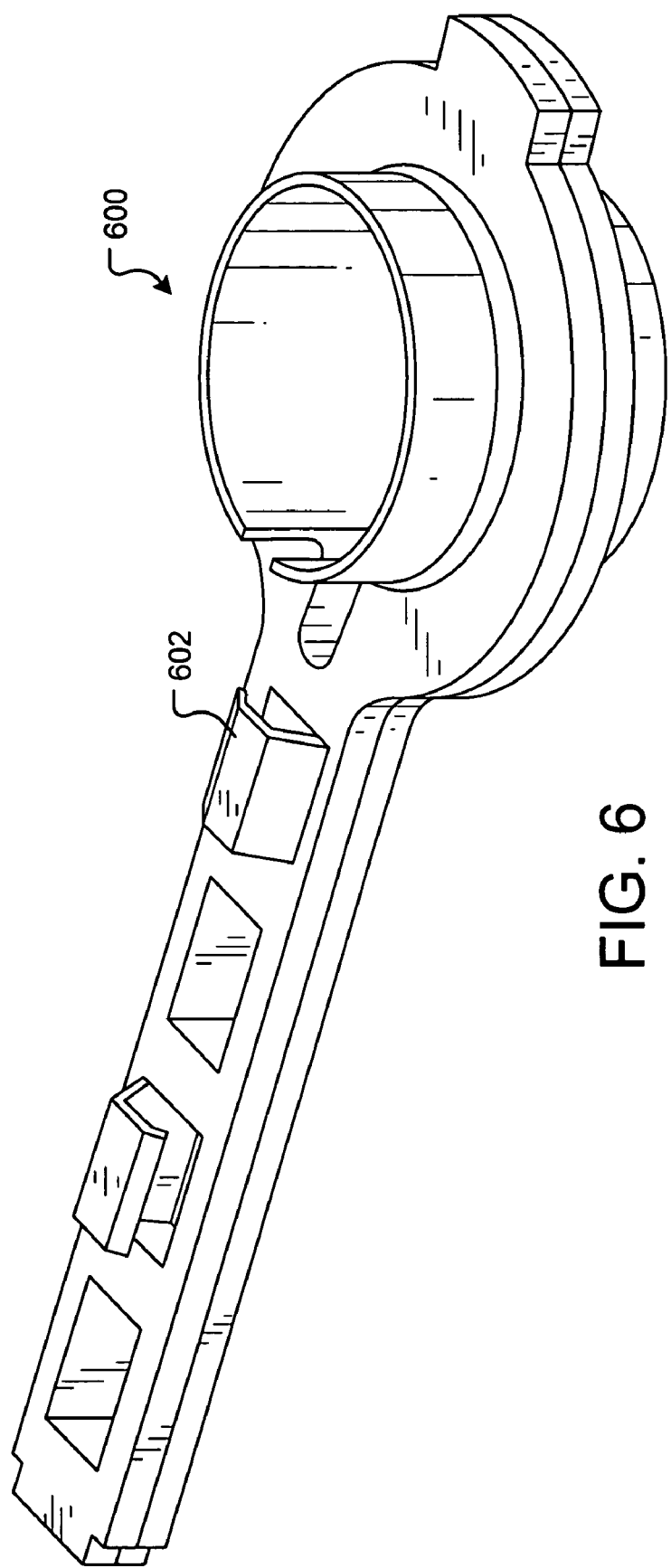
FIG. 6 depicts the apparatus shown in FIGS. 2a and 2b in accordance with an alternative embodiment of the present invention.

It will be clear that the present invention is well adapted to attain the ends and advantages mentioned, as well as those inherent therein. While a presently preferred embodiment has been described for purposes of this disclosure, various changes and modifications may be made which are well within the scope of the present invention. For example, the conductivity probe 300 described as being constructed in accordance with the present invention includes a thermo sensor 320. Accordingly, the process for constructing this probe 300 illustrated in FIGS. 3 and 4 includes an action 402 of setting the thermo sensor 320 within the cavity 214 of the skeleton 200. In an alternative embodiment, however, the conductivity probe 300 may be constructed without the thermo sensor 320. Furthermore, the channel guides 210 on the neck 206 of the skeleton 200 may be alternatively be replaced with straps 602 operable to perform the same function of securing connection leads (e.g., 310, 316 and 322) to the neck 206. A skeleton 600 constructed in accordance with this alternative embodiment (i.e., having strap 602 rather than wiring channels 212) is shown in FIG. 6.

Numerous other changes may be made which will readily suggest themselves to those skilled in the art and which are encompassed in the spirit of the invention disclosed and as defined in the appended claims.

What is claimed is:

1. An apparatus for forming a conductivity probe having a first toroid and a second toroid, the apparatus comprising:
   a toroid keeper having an upper annulus, a lower annulus, and a spacer separating the upper annulus from the lower annulus, wherein the upper annulus is sized to hold the first toroid on the keeper and wherein the lower annulus is sized to hold the second toroid on the keeper; and
   an elongated neck having a proximal end coupled to the toroid keeper and a distal end extending from the toroid keeper, the elongated neck further including an upper surface that carries wiring from the first toroid from the proximal end to the distal end, and a lower surface that carries wiring from the second toroid from the proximal end to the distal end.

2. An apparatus as defined in claim 1, wherein the elongated neck comprises:
   at least two wiring guides on the upper surface forming a first wiring channel therebetween, the first wiring channel operable to route wiring from the first toroid to the distal end when the first toroid is set around the upper annulus; and
   at least two wiring guides on the lower surface forming a second wiring channel therebetween, the second wiring channel operable to route wiring from the second toroid to the distal end when the second toroid is set around the lower annulus.

3. An apparatus as defined in claim 1, wherein the elongated neck comprises:
   a first wiring strap on the upper surface operable to route wiring from the first toroid to the distal end when the first toroid is set around the upper annulus; and
   a second wiring strap on the lower surface operable to route wiring from the second toroid to the distal end when the second toroid is set around the lower annulus.

4. An apparatus as defined in claim 1, wherein the spacer comprises an inner circumference and an outer circumference and wherein the upper annulus and the lower annulus each have an inner surface and an outer surface, the inner surface of the upper annulus and the inner surface of the lower annulus each having a diameter greater than or substantially equal to a diameter of the inner circumference such that a fluid passageway is formed in the toroid keeper.

5. An apparatus as defined in claim 1, wherein the spacer comprises:
   a notch operable to hold a thermo sensor between the first toroid and the second toroid.

6. An apparatus as defined in claim 1, wherein the first toroid and the second toroid each have an inner circumference and an outer circumference, and wherein the upper annulus and the lower annulus each have an inner surface and an outer surface, the upper annulus being sized such that the inner circumference of the first toroid contacts the outer surface of the upper annulus over at least 180 radial degrees and the lower annulus being sized such that the inner circumference of the second toroid contacts the outer surface of the lower annulus over at least 180 radial degrees.

7. A conductivity probe comprising:
   a first magnetic circuit having an inner circumference and an outer circumference;
   a second magnetic circuit having an inner circumference and an outer circumference;
   a keeper having an upper portion with an inner surface and an outer surface, a lower portion with an inner surface and an outer surface, and a spacer separating the upper portion from the lower portion, wherein the first magnetic circuit is situated around the upper portion such that the inner circumference of the first magnetic circuit contacts the outer surface of the upper portion and wherein the second magnetic circuit is situated around the lower portion such that the inner circumference of the second magnetic circuit contacts the outer surface of the lower portion; and an elongated neck having a proximal end coupled to the spacer, the elongated neck further including an upper surface that carries wiring from the first magnetic circuit from the proximal end to a distal end of the elongated neck, and a lower surface that carries wiring from the second magnetic circuit from the proximal end to the distal end of the elongated neck.

8. A conductivity probe as defined in claim 7, further including at least two wiring guides on the upper surface forming at least one wiring channel therebetween, wherein wiring from the first magnetic circuit is routed in the wiring channel to the distal end of the elongated neck.

9. A conductivity probe as defined in claim 7, wherein the elongated neck comprises a notch located on the distal end, the conductivity probe further comprising:

means for securing wiring from the first magnetic circuit and second magnetic circuit to the notch.

10. A conductivity probe as defined in claim 7, wherein the spacer comprises a notch, the conductivity probe further comprising:

a thermo sensor operable to measure temperature of a fluid environment in which the keeper is submerged, wherein the thermo sensor is located in the notch and is secured within the keeper between the first magnetic circuit and the second magnetic circuit.

11. A conductivity probe as defined in claim 7, wherein the magnetic circuits are toroidal in shape and wherein the upper portion and the lower portion are annuli, the spacer comprising an inner circumference and an outer circumference, the inner surface of the upper portion and the inner surface of the lower portion each having a diameter greater than or substantially equal to a diameter of the inner circumference of the spacer such that a fluid passageway is formed in the keeper.

12. A conductivity probe as defined in claim 7, further comprising:

an electrically transparent molding covering at least the first magnetic circuit, the second magnetic circuit and the keeper.

13. A conductivity probe as defined in claim 7, further comprising:

an electrically transparent housing covering at least the first magnetic circuit, the second magnetic circuit and the keeper.

14. A conductivity probe as defined in claim 7, wherein the magnetic circuits are toroidal in shape and wherein the upper and lower portions are annuli.

15. A conductivity probe as defined in claim 14, wherein the inner circumference of the first magnetic circuit contacts the outer surface of the upper portion over at least 180 radial degrees and wherein the second magnetic circuit is situated around the lower portion such that the inner circumference of the second magnetic circuit contacts the outer surface of the lower portion over at least 180 radial degrees.

* * * * *